United States Patent [19]
Zudkevitch et al.

[11] 4,455,198
[45] Jun. 19, 1984

[54] EXTRACTION AND/OR EXTRACTIVE DISTILLATION OF ETHANOL FROM AQUEOUS SOLUTIONS

[75] Inventors: David Zudkevitch, Denville; David K. Preston, Hope; Stephen E. Belsky, Parsippany, N.J.

[73] Assignee: Allied Corporation, Morris Township, Morris County, N.J.

[21] Appl. No.: 444,925

[22] Filed: Nov. 26, 1982

Related U.S. Application Data

[63] Continuation-in-part of Ser. No. 276,302, Jun. 22, 1981, abandoned.

[51] Int. Cl.$^3$ .......................... B01D 3/34; B01D 3/40
[52] U.S. Cl. ........................................ 203/19; 203/39; 203/62; 203/63
[58] Field of Search ...................... 203/19, 54, 55, 62, 203/63, 39, 43–46, 39; 568/913, 917, 918

[56] References Cited

U.S. PATENT DOCUMENTS 2,537,115  1/1951  Scheibel ............................... 203/62
2,591,671  4/1952  Catterall .............................. 203/19

Primary Examiner—Frank Sever
Attorney, Agent, or Firm—Alan M. Doernberg; Gerhard H. Fuchs; Kenneth E. Stroup, Jr.

[57] ABSTRACT

Ethanol is concentrated from ethanol-water mixtures by extraction or extractive distillation with a solvent which is a cyclic ketone of at least seven carbons or cyclic alcohol of at least eight carbons such a cyclohexylcyclohexanone or cyclohexylcyclohexanol. In the extractive distillation process, a first overheads is produced which can be made to be steam with minimal ethanol content and a second overhead is produced which can be made to be essentially pure ethanol. The preferred solvents are also non-toxic, such that the alcohol can be used for human consumption.

22 Claims, 2 Drawing Figures

EXTRACTION AND/OR EXTRACTIVE DISTILLATION OF ETHANOL FROM AQUEOUS SOLUTIONS

This is a continuation in part of application Ser. No. 6/276,302, filed 6/22/81, now abanoned.

BACKGROUND OF THE INVENTION

The concentration of ethanol from aqueous solutions has been accomplished by distillation for many years in the production of alcoholic beverages, solvents and a variety of chemicals. Ethanol from such distillations, either alone or in combination with hydrocarbon fuels such as gasoline, has been more recently used as an automotive fuel. Contamination by water is an undesired consequence of most simple fractional distillation schemes when the alcohol is to be used as a fuel, while contamination with toxic materials is an undesired consequence when the alcohol is to be used for human consumption. In both processes, the high energy requirements for the distillation, coupled with the inherent limitation imposed by the ethanol-water azeotrope have caused various methods other than simple distillation to be investigated.

Extraction of aqueous ethanol solutions by an organic solvent has been proposed, with the extract containing both ethanol and solvent then generally being distilled to separate the product ethanol and a recycle solvent. An article by J. W. Roddy, entitled "Distribution of Ethanol-Water Mixtures to Organic Liquids" in Ind. Eng. Chem. Process Des. Dev., volume 20, pp 104–108 (1981) indicates that a wide variety of organic solvents have been used for such extractions, but that the number of solvents having distribution coefficients greater than 0.5 for ethanol and separation factors greater than 10 from aqueous solutions (as defined in the Roddy article) are quite limited. The article indicates the general order of extraction for ethanol to be hydrocarbon=halocarbon<ether<ketone<amine<ester<alcohol=phosphate. The best candidate identified in the article were 2-ethyl-1-butanol, having a distribution coefficient of 0.69 for ethanol and a separation factor of 30. The next best candidate, triisobutyl phosphate, had a distribution factor for ehtanol of 0.65 and a separation factor of 10.

It has also been proposed to conduct a distillation to separate ethanol from water with an additional solvent being added to the system so as to either enhance the separation and purity of ethanol as the overhead and of water as the bottoms, or to reverse the volatilities for ethanol and water, causing water to be removed as top product, and ethanol mixed with solvent to be removed as bottom product. Examples of such suggestions are contained in U.S. Pat. No. 2,591,672 (with a hydrocarbon as the extractive distillation solvent) and and article by C. Black entitled "Distillation Modeling of Ethanol Recovery and Dehydration Processes for Ethanol and Gasohol", in *Chem. Eng. Prog.*, September 1980, pp 78–85, especially at pp 82–84.

While the above references indicate the desirability of extraction and extractive distillation schemes to recover ethanol from aqueous solutions, there is still a need for solvents suitable for such extraction and extractive distillation.

BRIEF DESCRIPTION OF THE INVENTION

The present invention includes a process which comprises the steps:

(a) distilling a feed mixture comprising water and ethanol with a solvent comprising a cyclic ketone of at least seven carbons or cyclic alcohol of at least eight carbons to produce a first overhead stream consisting essentially of water and a first bottoms stream consisting essentially of ethanol and solvent, and (b) distilling the first bottom stream to produce an overhead stream consisting essential of ethanol and a bottoms stream consisting essentially of solvent. Typically, the feed mixture contains about equal amounts of water and ethanol, while the first overheads is at least 90 weight percent water and the second overheads contains at least about 95 weight percent ethanol, and preferably contains more ethanol than the ethanol-water azeotrope at the operating pressure of the second distillation. It is possible by this process to produce essentially pure water or steam as the first overheads, to produce ethanol of greater than 99 percent purity as the second overheads and, with proper selection of solvent, apparatus and process conditions, to avoid the introduction of toxic impurities into the ethanol produced as the second overhead stream.

DETAILED DESCRIPTION OF THE INVENTION

The present invention includes extraction and extractive distillation processes for separating an ethanol-rich stream from a mixture of ethanol and water. Either the extraction solvent employed in the extraction process or the extractive distillation solvent employed in the extractive distillation process may be cyclic ketones of at least seven carbons. Suitable monocyclic ketones include alkylcyclohexanones or cycloheptanone, cyclooctanone or the like, or any of them substituted or further substituted by alkyl or other non-reactive substituents. Preferred, however, are such monocyclic ketones substituted by cycloalkyl or by aryl, and particularly by cyclohexyl or phenyl. The most preferred ketones are cyclohexylcyclohexanone and phenylcyclohexanone (any position isomer or mixture of isomers being suitable).

Alternatively, the solvent for either process may be a cyclic alcohol of at least eight carbons such as an alkycyclohexanol, cyclooctanol or the like, or any of these substituted or further substituted by alkyl or other non-reactive substitutents. The most preferred alcohols are cyclohexylcyclohexanol and phenylcyclohexanol.

The alcohol or ketone may be a relatively small (or light) material such as methylcyclohexanone (b.p. 168° C.), cycloheptanone (b.p. 179° C.), propyl cyclohexanone (b.p. 195° C.), ethylcyclohexanol (b.p. 160° or 181° C.), cyclooctanol, cyclooctanone (b.p. 196° C.) dimethylcyclohexanol or dimethylcyclohexanone. Preferred, however, the are the medium and higher boiling cyclic alcohols or ketones of atmospheric boiling points at least about 190° C., and preferably at least about 210° C. The most preferred materials, phenylcyclohexanol, phenylcyclohexanone, cyclohexylcyclohexanol and cyclohexylcyclohexanone, having boiling points in the general range of 250°–290° C. The use of higherboiling solvents gives better separation of ethanol from water in the first extraction or distillation, and also gives easier separation of alcohol from solvent in the subsequent distillation. Results are particularly superior to any of the linear aliphatic alcohol solvents contemplated by U.S. Pat. No. 2,591,671 to Caterall.

It is contemplated that the solvent containing principally cyclic ketone or alcohol may also contain a minor proportion of the other, or of acyclic ketones or alcohols such as tridecylketone or other long chain aliphatic ketones or alcohols, preferably of 7–20 carbons.

One source of such cycloalkylcyclohexanones is as a by-product of phenol hydrogenation, as described in U.S. Pat. No. 4,187,152 of Roth et al. (Feb. 5, 1980), which employs the preferred ketones as extractive distillation agents for separating cyclohexanone and cyclohexanol from phenol. In such source, the ketones will normally be found in mixtures with the corresponding alcohol, i.e. cyclohexylcyclohexanol and phenylcyclohexanol (primarily the former).

In the extraction process of the present invention, mixtures of ethanol and water such as 8–70 (preferably 40–60) weight percent ethanol and 30–92 (preferably 40–60) weight percent water are contacted with the extractant in single or multiple stages, or preferably in countercurrent flow (e.g. through a packed or tray column). The raffinate contains water with relatively little ethanol, depending upon the solvent, effective number of stages, ratios of mixture to extractant, temperature and other conditions. Essentially no solvent will be found in the raffinate. The extract will contain solvent and ethanol with relatively little water. Ethanol can be separated from the solvent by distillation with solvent recycled.

The extractive distillation process of the present invention involves the distillation (and preferably fractional distillation) of ethanol-water mixtures in the presence of added solvent. Typically, the ethanol-water mixture is fed to an intermediate point of a tray or packed column, the solvent is fed to a higher tray; and suitable processing rates, temperature and pressure conditions and reflux ratios are employed. The overheads of this first distillation contains water, with reduced amounts of ethanol, preferably at least 90 weight percent water and more preferably at least 99 weight percent water. The bottoms contains solvent and ethanol, preferably with minimal amounts of water. Subsequent distillation of this bottoms (preferably fractional distillation) produces a second overhead high in ethanol (preferably at least 95 weight percent ethanol). When the extractive distillation solvent is one of the aryl- or cycloalkylcyclohexanones, or the corresponding alcohols, the second overhead will contain no measurable solvent, but only ethanol and minor amounts of water. Both distillation steps may be conducted at atmospheric pressure, but it is preferred to operate the second distillation step below atmospheric pressure, for example between 1 and 50 kPa. Regardless of the pressure chosen for the second step, ethanol concentrations obtainable will exceed the proportion of ethanol in the ethanol-water azeotrope at the distillation pressure, and thus be greater than could be achieved by simply distilling the feed mixture in a conventional fashion at this pressure with a very large number of effective trays and with high reflux ratios.

The feed mixture to either the extraction process or the extractive distillation process may contain other materials in addition to ethanol and water. It is preferred, however, to feed mixtures such as are generated by distilling fermentation mixtures in a "beer still" which produces a product consisting essentially of water and ethanol. Minor impurities which may be present include "fusel oil" (amyl alcohols, aldehydes and similar materials) which will be present in the extract in the present extraction process and in the second bottoms in the extractive distillation process. In either case, fusel oil and similar contaminations may be bled from the system by subjecting the solvent or a portion thereof to a treatment such a further low-pressure distillation to reduce the impurity concentration.

Figure 1:
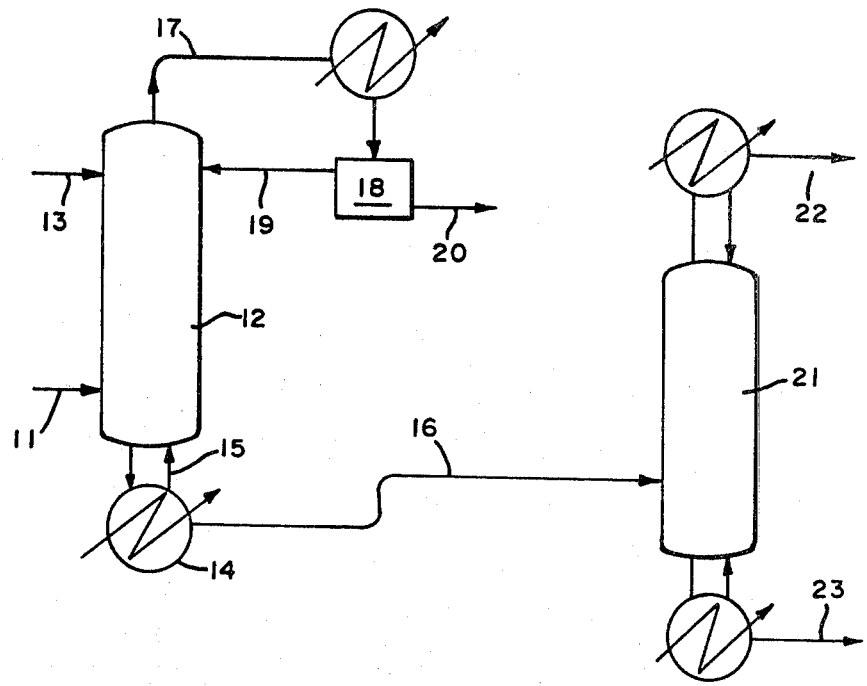
FIG. 1 illustrates the extractive distillation process of the present invention.

An ethanol-water mixture (e.g. 50:50 mixture by weight) is fed in stream 11 to a packed or tray column 12. At a point above the point where stream 11 is fed, a solvent stream (e.g. cyclohexylcyclohexanone) is fed to column 12. The bottoms of the column are heated by direct or indirect steam heating or other heating means in reboiler 14, with a portion returned in stream 15 and a portion fed forward in stream 16. The overheads 17 are condensed and collected in vessel 18 (which may include means for phase separation), with a portion (including especially any separate organic layer) recycled in stream 19 to near the top of column 12 and a portion removed as first overheads 20. With proper adjustment of reflux ratio (stream 19 divided by stream 20), feed temperatures, system pressure, feeds ratio and number of effective tray in column 12, one can adjust the operation to achieve the desired water concentration (preferably over 90%, more preferably over 99%) in first overheads 20. Furthermore, the water content of stream 16 can be reduced to a low proportion (e.g. under 5% and preferably much lower) of the ethanol content of stream 16.

Stream 16 is fed to a second column 21 which preferably operates at subatmospheric pressure. While an overhead 22 may be taken without flux, it is preferred to have low reflux ratios. The bottoms from second column 21 are removed in stream 23.

It is contemplated to use a variety of standard engineering devices known to the distillation art in practicing the present invention. Thus, for example, streams 20, 22, and 23 may be passed, as appropriate, in heat exchange with other streams for cooling or heating, preferably prior to passage in heat exchange with cooling water, steam or other process streams. Furthermore, if the present process is combined with operation of a beer still to produce stream 11, heat exchange between various streams in the present process and streams of the beer still are also contemplated.

The solvent in stream 23 may be cooled and returned in stream 13 or the solvent, or any portion thereof, may be treated (e.g. by vacumn distillation) to remove any built up fusel oil or other impurities.

Figure 2:
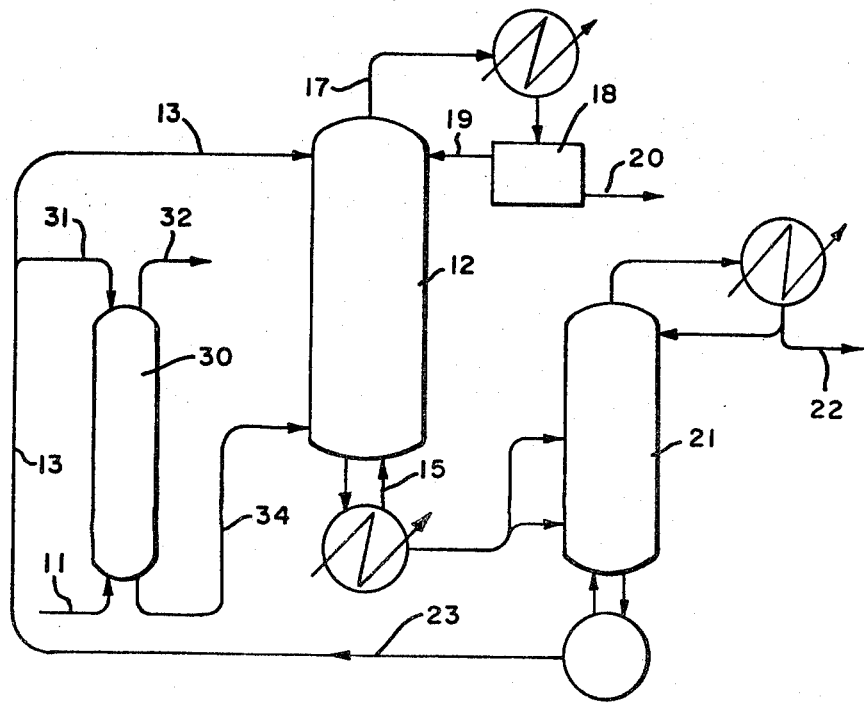
FIG. 2 illusrates extraction and extractive distillation.

FIG. 2 illustrate a combination of the extraction method of the present invention with the extractive distillation method of the present invention. Feed mixture 11 (e.g. 50:50 ethanol-water) is fed to the bottom of packed column 30 where it is passed in countercurrent contact with solvent fed into the top of the column in stream 31. The raffinate containing water and minor organic content is removed from the top of column 30 in stream 32. The extract containing mainly solvent and ethanol, with a minor water content, is removed from the bottom of extraction column 30 in stream 34 and fed to distillation column 12. Column 12 is operated as described above for FIG. 1 except that, with the lowered water level, higher reflux ratios are employed. Thus the water removed in stress 20 of FIG. 2 is reduced compared to stream 20 of FIG. 1 by approximately the amount of water removed in stream 32. Accordingly, this embodiment is especially suitable with feed mixtures 11 having more water than ethanol. The feed of solvent in stream 31 should be sufficiently high compared to ethanol in stream 11 for the density of extract in stream 34 to remain greater than the density of ethanol-water in stream 11.

The bottoms 16 are fed from reboiler 14 of column 12 to column 21, which preferably operates at subatmospheric pressure. Overhead 22 is rich in ethanol while bottoms 23 is very rich in solvent. The solvent in stream 23 may be recycled into streams 31 and 13, optionally after a seperate distillation to purge fusel oil.

To practice a simple extraction process, one need only feed stream 34 in FIG. 2 directly to column 21, providing an ethanol rich overheads 22 and a solvent recycle stream 23. In such a scheme, both reflux and reboil should be employed on column 21 in conventional fashion.

EXAMPLE 1

Cyclohexylcyclohexanone was mixed with mixtures of ethanol and water in mixing ratios, by weight, as indicated in Table 1. In Table 1, the first ratio is ethanol to water; the second is solvent to ethanol plus water. After vigorous agitation, the phases were permitted to separate into an upper aqueous layer and a lower organic layer. Both were sampled and analyzed by gas chromatography, with the results as displayed in Table 1. These represented a distribution coefficient for ethanol (its concentration in the organic layer divided by its concentration in the aqueous layer) as indicated in Table 1. The separation factor for the solvent is also indicated in Table 1.

Runs A, B and C were conducted at 25° C.; runs D and E were conducted at 72° C.,

TABLE 1

Extraction of Ethanol-Water Mixture by Cyclohexylcyclhexanone

| Run (Phase) | Mix Ratios E/W | Mix Ratios S/(E+W) | Mole % Ethanol | Mole % Water | Mole % Solvent | Separation Coef. | Dist. Coef. |
|---|---|---|---|---|---|---|---|
| A (upper) | 1 | 7.83 | 9.43 | 90.55 | 0.02 | 24.1 | 0.217 |
| A (lower) | | | 14.88 | 5.93 | 79.19 | | |
| B (upper) | 0.11 | 1.57 | 4.73 | 1.43 | 93.84 | 105.6 | 0.169 |
| B (lower) | | | 3.08 | 96.91 | 0.01 | | |
| C (upper) | 0.72 | 1.39 | 15.96 | 83.97 | 0.07 | 10.34 | 0.308 |
| C (lower) | | | 26.59 | 13.59 | 59.82 | | |
| D (upper) | 1.66 | 8.13 | 19.52 | 9.67 | 70.81 | 26.09 | 0.394 |
| D (lower) | | | 7.20 | 92.77 | 0.03 | | |
| E (upper) | 0.41 | 3.79 | 15.73 | 5.65 | 78.62 | 47.6 | 0.362 |
| E (lower) | | | 5.56 | 94.36 | 0.08 | | |

It should be noted that the aqueous phase was upper in runs A and C and lower in runs B, D and E because of the close densities of the materials.

A comparision of these values with values reported in the Roddy article cited above illustrates the effectiveness of the present solvents for extraction of ethanol from ethanol/water mixtures.

EXAMPLE 2

A mixture of 22.2 mole % ethanol and 77.8 mole % water ("Feed 1") was continuously fed to the fifth tray, counted from the reboiler, of a distillation assembly consisting of a reboiler, 35 trays, a condenser and a reflux splitter. Cyclohexylcyclohexanone (essentially all the 2-isomer) ("Feed 2") was fed continuously onto the 35th tray. The pressure was 747 mm of mercury (99.6 kPa) at the feed point for Feed 2 and was 865 mm of mercury (115.3 kPa) at the reboiler. The feed rates were 1.12 mol/h of Feed 1 and 4.0 mol/h for Feed 2. Condensed overheads contained 94.82 mole % water, 5.15 mol % ethanol and 0.03 mol % solvent. Bottoms contained 95.1 mol % solvent, 4.89 mol % ethanol and 0.01 mol % water. This Example is summarized in Table 2.

EXAMPLE 3

In another distillation-stripper column, a mixture of ethyl alcohol and solvent of composition similar to that of the bottoms of Example 2 are fed continuously onto the tenth tray of a column consisting of a reboiler, 22 trays, a condenser, and a reflux splitter. The products from that continuous run at subatmospheric pressure at the condenser are as shown in Table 3, indicating that virtually all of the ethyl alcohol can be recovered as overhead vapor consisting of 99.9 mole % ethyl alcohol. Virtually all the solvent which is introduced as distillation "Feed 2" in Example 2 and subsequently the feed to the second column (stripper) is recovered as the bottoms from the stripper column.

TABLE 2

| | Extractive Dehydration | | | |
|---|---|---|---|---|
| Compound | Feed 1 | Feed 2 | Overhead | Bottoms |
| Tray No. from Bottom | 5 | 35 | 35 (vapor) | 0 |
| Ethanol | 22.2% | 0 | 5.15% | 4.89% |
| Solvent | 0 | 100% | 0.03% | 95.1% |
| Water | 77.8% | 0 | 94.82% | 0.01% |
| Pressure (kPa) | 102.0 | 99.6 | 99.6 | 115.3 |
| Rate (mol/h) | 1.12 | 4.0 | 0.92 | 4.2 |

TABLE 3

| | RECOVERY (0.5 REFLUX RATIO) | | |
|---|---|---|---|
| Compound | Feed | Overhead | Bottoms |
| Tray No. From Bottom | 7 | 22 | 0 |
| Ethanol | 11.67% | 99.915% | 0.004% |
| Solvent | 87.59% | 0.0% | 99.996% |
| Water | 0.01% | 0.085% | 0.0% |
| Pressure (kPa) | 16.0 | 13.3 | 19.2 |
| Rate (mol/h) | 75 | 15 | 60 |

EXAMPLE 4

Vapor liquid equilibrium data (in mol %) were collected for various alcohol solvents in admixture with water and ethanol to determine their efficiencies as extractive distillation agents in the present process. Hexanol was chosen as representing the highest-boiling alcohol contemplated by U.S. Pat. No. 2,591,671 to Caterall; 3-methylcyclohexanol was chosen as an intermediate material (not presently claimed) and 2-ethylcyclohexanol (b.p. 181° C.) was selected as representing the smallest solvent presently claimed (eight carbons). The eight points shown in Table 4 represent hexanol (A-C), 3-methylcyclohexanol or 3-MCH (D-E) and 2-ethylcyclohexanol or 2-ECH (F-H).

TABLE 4

| Run | | Ethanol | Solvent | Water |
|---|---|---|---|---|
| A | Liq. Phase | 0.086 | 0.868 | 0.046 |
|   | Vapor Phase | 0.422 | 0.205 | 0.373 |
| B | Liq. Phase | 0.081 | 0.876 | 0.043 |
|   | Vapor Phase | 0.427 | 0.203 | 0.371 |
| C | Liq. Phase | 0.080 | 0.882 | 0.039 |
|   | Vapor Phase | 0.429 | 0.195 | 0.376 |
| D | Liq. Phase | 0.080 | 0.876 | 0.044 |
|   | Vapor Phase | 0.447 | 0.165 | 0.388 |
| E | Liq. Phase | 0.712 | 0.894 | 0.034 |
|   | Vapor Phase | 0.450 | 0.199 | 0.351 |
| F | Liq. Phase | 0.078 | 0.885 | 0.036 |
|   | Vapor Phase | 0.505 | 0.059 | 0.436 |
| G | Liq. Phase | 0.066 | 0.903 | 0.032 |
|   | Vapor Phase | 0.488 | 0.090 | 0.422 |
| H | Liq. Phase | 0.056 | 0.916 | 0.028 |
|   | Vapor Phase | 0.455 | 0.139 | 0.405 |

The pressure and temperature for these eight runs (each simulating the plate in the column 12 of FIG. 1 where solvent is introduced) and the vapor/liquid mole ratio ($k_e$ for ethanol and $k_w$ for water) are shown in Table 5. The final value, $k_w/k_e$, represents a figure of merit for the solvent.

TABLE 5

| Run | Solvent | Temp | Pressure (kpa) | $k_e$ | $k_w$ | $k_w/k_e$ |
|---|---|---|---|---|---|---|
| A | Hexanol | 96° C. | 39.46 | 4.93 | 8.04 | 1.63 |
| B | Hexanol | 96° C. | 38.92 | 5.27 | 8.66 | 1.64 |
| C | Hexanol | 96° C. | 38.92 | 5.40 | 9.68 | 1.79 |
| D | 3-MCH | 96° C. | 33.33 | 5.57 | 8.90 | 1.60 |
| E | 3-MCH | 96° C. | 33.46 | 6.32 | 10.21 | 1.61 |
| F | 2-ECH | 94° C. | 33.86 | 6.41 | 12.14 | 1.90 |
| G | 2-ECH | 96° C. | 31.59 | 7.41 | 13.40 | 1.81 |
| H | 2-ECH | 96° C. | 25.06 | 8.10 | 14.74 | 1.82 |

We claim:

1. A method for the concentration of ethanol which comprises the steps:
   (a) distilling a feed mixture consisting essentially of water and ethanol with a solvent comprising a cyclic ketone of at least seven carbons or cyclic alcohol of at least eight carbons to produce a first overhead stream consisting essentially of water and a first bottoms stream consisting essentially of ethanol and solvent, and
   (b) distilling the first bottoms stream to produce an overhead stream consisting essential of ethanol and a bottoms stream consisting essentially of solvent.

2. The method of claim 1 wherein said feed mixture consists essentially of water, ethanol and solvent.

3. The method of claim 2 wherein said feed mixture is the extract from the extraction of a second mixture consisting essentially of water and ethanol by the solvent.

4. The method of claim 1 wherein the solvent comprises a cyclic ketone.

5. The method of claim 4 wherein said cyclic ketone is cyclohexylcyclohexanone.

6. The method of claim 4 wherein said cyclic ketone is phenylcyclohexanone.

7. The method of claim 1 wherein said feed mixture contains about 8-70 weight percent ethanol and about 30-92 weight percent water.

8. The method of claim 7 wherein said feed mixture contains about 40-60 weight percent ethanol and about 40-60 weight percent water.

9. The method of claim 7 wherein the first overheads stream contains at least about 90 weight percent water and the second overhead stream contains at least about 95 weight percent ethanol.

10. The method of claim 9 wherein the second overhead stream contains a greater ethanol weight proportion than the ethanol weight proportion in the ethanol-water azeotrope at the operating pressure of the distillation step b.

11. The method of claim 9 wherein each distillation step is conducted at atmospheric pressure.

12. The method of claim 9 wherein said distillation step a is conducted at atmospheric pressure and said distillation step b is conducted below atmospheric pressure.

13. The method of claim 1 wherein the solvent comprises mixtures of cyclohexylcyclohexanol and cyclohexylcyclohexanone.

14. The method of claim 13 wherein the solvent further comprises an aliphatic acyclic ketone of 7-20 carbons.

15. The method of claim 1 wherein said solvent has a boiling point of at least about 190° C.

16. The method of claim 1 wherein said solvent has a boiling point of at least about 210° C.

17. A method for the concentration of ethanol which comprises extracting a feed mixture consisting essentially of ethanol and water with a solvent comprising a cyclic ketone of at least seven carbons or cyclic alcohol of at least eight carbons to produce a raffinate comprising water and an extract consisting essentially of solvent and ethanol, and distilling the extract to produce an overheads consisting essentially of ethanol and a bottoms consisting essentially of solvent.

18. The method of claim 12 wherein the solvent comprises a cyclic ketone.

19. The method of claim 18 wherein said cyclic ketone is cyclohexylcyclohexanone.

20. The method of claim 18 wherein said cyclic ketone is phenylcyclohexanone.

21. The method of claim 17 wherein the solvent comprises mixtures of cyclohexylcyclohexanol and cyclohexylcyclohexanone.

22. The method of claim 21 wherein the solvent further comprises an aliphatic acyclic ketone of 7-20 carbons.

* * * * *